(12) United States Patent
Zhang et al.

(10) Patent No.: US 9,423,357 B2
(45) Date of Patent: Aug. 23, 2016

(54) OBLIQUE ILLUMINATOR FOR INSPECTING MANUFACTURED SUBSTRATES

(71) Applicant: KLA-Tencor Corporation, Milpitas, CA (US)

(72) Inventors: Shiyu Zhang, Hayward, CA (US); Charles N. Wang, Santa Clara, CA (US); Yevgeniy Churin, San Jose, CA (US); Yong-Mo Moon, San Ramon, CA (US); Hyoseok Daniel Yang, Santa Clara, CA (US); Mark S. Wang, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 169 days.

(21) Appl. No.: 14/288,622

(22) Filed: May 28, 2014

(65) Prior Publication Data

US 2014/0299779 A1    Oct. 9, 2014

Related U.S. Application Data

(62) Division of application No. 13/257,441, filed as application No. PCT/US2011/045366 on Jul. 26, 2011, now Pat. No. 8,794,801.

(60) Provisional application No. 61/369,625, filed on Jul. 30, 2010.

(51) Int. Cl.
*F21V 7/09* (2006.01)
*G01N 21/88* (2006.01)
*G01N 21/95* (2006.01)

(52) U.S. Cl.
CPC ........ *G01N 21/8806* (2013.01); *G01N 21/9501* (2013.01)

(58) Field of Classification Search
CPC .......... G01N 21/9501; G01N 21/8806; G01N 2021/8809
See application file for complete search history.

(56) References Cited

U.S. PATENT DOCUMENTS

| | | | | |
|---|---|---|---|---|
| 4,518,232 A | * | 5/1985 | Dagenais | B23K 26/073 219/121.74 |
| 5,486,919 A | * | 1/1996 | Tsuji | G01N 21/88 356/237.4 |
| 6,356,700 B1 | * | 3/2002 | Strobl | G02B 6/0006 359/859 |
| 6,512,579 B2 | * | 1/2003 | Oomori | G01N 21/956 356/237.5 |
| 6,847,443 B1 | * | 1/2005 | Herod | G01N 21/956 250/559.27 |
| 7,828,448 B2 | * | 11/2010 | Kim | F21K 9/00 348/771 |
| 7,964,858 B2 | * | 6/2011 | Yang | B82Y 10/00 250/455.11 |
| 2004/0207836 A1 | * | 10/2004 | Chhibber | G01N 21/4738 356/237.4 |
| 2006/0274432 A1 | | 12/2006 | Jeong | |
| 2008/0137345 A1 | * | 6/2008 | Wimberly | F21V 3/04 362/299 |
| 2009/0059236 A1 | * | 3/2009 | Meeks | G01B 11/065 356/445 |
| 2010/0060867 A1 | * | 3/2010 | Li | G03B 21/208 353/99 |

FOREIGN PATENT DOCUMENTS

JP    10-311801    11/1998

* cited by examiner

*Primary Examiner* — Peggy Neils
(74) *Attorney, Agent, or Firm* — Okamoto & Benedicto LLP

(57) ABSTRACT

One embodiment relates to an oblique illuminator. The oblique illuminator includes a light source emitting a light beam, a first reflective surface, and a second reflective surface. The first reflective surface has a convex cylindrical shape with a projected parabolic profile along the non-powered direction which is configured to reflect the light beam from the light source and which defines a focal line. The second reflective surface has a concave cylindrical shape with a projected elliptical profile which is configured to reflect the light beam from the first reflective surface and which defines first and second focal lines. The focal line of the first reflective surface is coincident with the first focal line of the second reflective surface. The first and second focal lines of the second reflective surface may be a same line in which case the elliptical curvature is a projected spherical profile. Other embodiments, aspects and features are also disclosed.

12 Claims, 12 Drawing Sheets

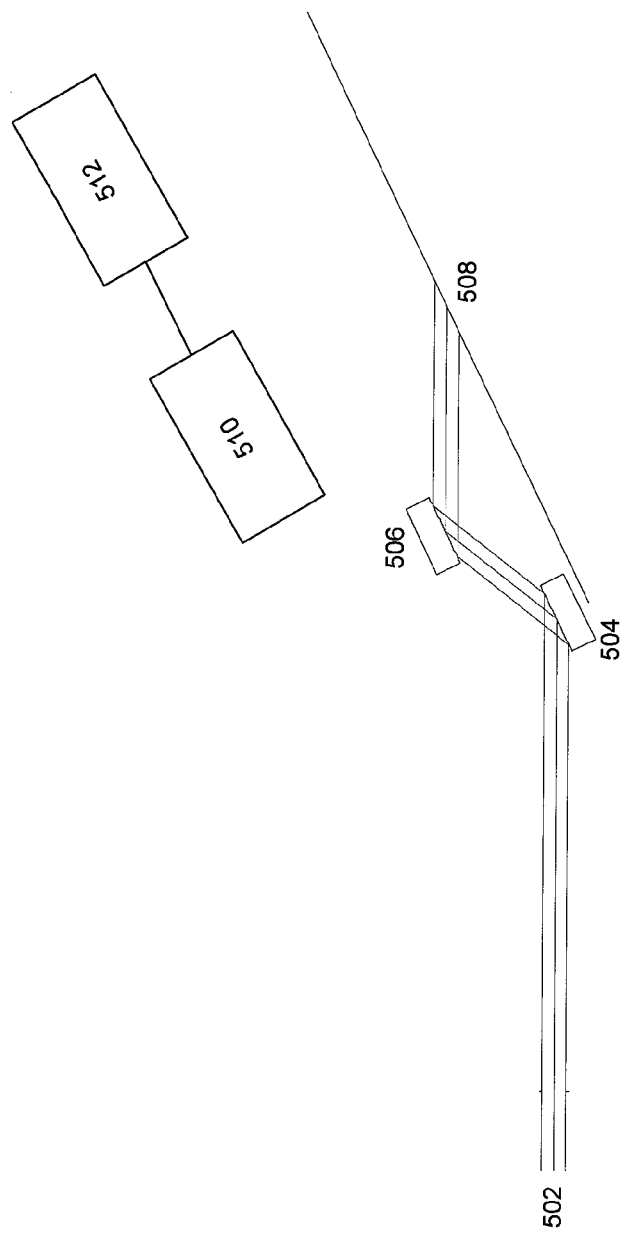

US 9,423,357 B2

OBLIQUE ILLUMINATOR FOR INSPECTING MANUFACTURED SUBSTRATES

CROSS-REFERENCE TO RELATED APPLICATION(S)

The present application is a divisional application of U.S. patent application Ser. No. 13/257,441 which is a 371 application (national stage entry date Sep. 19, 2011) of International Patent Application No. PCT/US2011/045366, filed Jul. 26, 2011, the disclosure of which is hereby incorporated by reference. International Patent Application No. PCT/US2011/045366 claims the benefit of provisional U.S. Patent Application No. 61/369,625, filed Jul. 30, 2010, the disclosure of which is hereby incorporated by reference.

BACKGROUND OF THE INVENTION

1. Technical Field

The present disclosure relates to apparatus and methods for providing illumination. More particularly, the present disclosure relates to apparatus and methods for providing oblique illumination for use, for example, in the inspection of manufactured substrates.

2. Description of the Background Art

Inspection processes are used at various steps during a semiconductor manufacturing process to promote higher yield. However, as the dimensions of semiconductor devices decrease, the detection of defects of decreasing size has become necessary to avoid unwanted manufacturing errors in the devices.

One way to improve the detection of such very small defects is to increase the sensitivity of an optical inspection system. The sensitivity of an optical inspection system may be increased, for example, by using oblique illumination, instead of normal illumination.

SUMMARY

One embodiment relates to an oblique illuminator. The oblique illuminator includes a light source emitting a light beam, a first reflective surface, and a second reflective surface. The first reflective surface has a convex cylindrical shape with a projected parabolic profile along the non-powered direction of the cylinder which is configured to reflect the light beam from the light source and which defines a virtual focal line. The first reflecting surface with such a profile may be referred to as a parabolic cylindrical reflecting surface. The second reflective surface has a concave cylindrical shape with projected elliptical profile which is configured to reflect the light beam from the first reflective surface and which defines first and second focal lines. The virtual focal line of the first reflective surface is coincident with the first focal line of the second reflective surface. The first and second focal lines of the second reflective surface may be a same line in which case the projected elliptical profile is a spherical one.

Another embodiment relates to a method of illuminating a line segment on a surface of a target substrate. A light beam is emitted from a light source. The light beam is reflected from a first reflective surface. The first reflective surface has a convex cylindrical shape with a projected parabolic profile which defines a focal line. The light beam is further reflected from a second reflective surface. The second reflective surface has a concave cylindrical shape with a projected elliptical profile which defines first and second focal lines. The virtual focal line of the first reflective surface is coincident with the first focal line of the second reflective surface.

Another embodiment relates to an apparatus for inspecting a target substrate. The apparatus includes an oblique illuminator and a detector. The oblique illuminator includes a light source emitting a light beam, a first reflective surface, and a second reflective surface. The first reflective surface has a convex cylindrical shape with a projected parabolic profile which is configured to reflect the light beam from the light source and which defines a focal line. The second reflective surface has a concave cylindrical shape with a projected elliptical profile which is configured to reflect the light beam from the first reflective surface and which defines first and second focal lines. The focal line of the first reflective surface is coincident with the first focal line of the second reflective surface, and the second focal line of the second reflective surface lies on a surface of the target substrate such that a line segment is illuminated on the surface of the target substrate.

One example of the target substrate may be a semiconductor wafer; and the manufactured substrates may refer to patterned wafers.

Other embodiments, aspects and features are also disclosed.

BRIEF DESCRIPTION OF THE DRAWINGS

FIG. 5 shows a projected view of a two-mirror broadband oblique illuminator for an optical inspection system in accordance with an embodiment of the invention.

DETAILED DESCRIPTION

Previous oblique (non-normal) illuminators have various drawbacks. One drawback is that previous oblique illuminators typically use cylindrical mirrors with spherical or aspherical cross-sections which produce residual aberrations. A corrective element may be introduced to correct for the residual aberrations, but the correction is generally not complete, the residual aberration will limit the increase in numerical aperture. Another drawback is that previous oblique illuminators are typically sensitive to the wavelength of the illumination. In other words, they are effectively narrowband due to wavelength dispersion through refractive or dispersive materials. Another drawback is that previous oblique illuminators are typically sensitive to misalignment of their optical elements. A small misalignment may substantially impact their optical performance.

Figure 1:
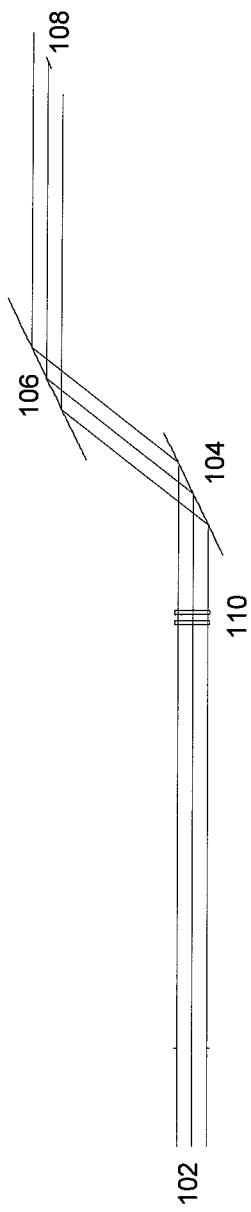
FIG. 1 is an optical system layout of a previous oblique illuminator for use in inspecting manufactured substrates.

FIG. 1 is an optical system layout of a previous oblique illuminator for use in inspecting manufactured substrates. Such a previous oblique illuminator is described in U.S. Pat. No. 7,199,946. This previous oblique illuminator includes a light source 102, a first mirror 104, and a second mirror 106.

The first and second mirrors (104 and 106, respectively) are cylindrical mirrors to form a narrow line beam illumination on the target 108. The axes of the cylindrical mirrors are parallel to the lines which represent the mirrors in the diagram. The cylindrical mirror pair produces residual aberrations. In order to correct for these aberrations, an aspherical cylindrical element (also called an acylinder element or an acylindrical element) 110 is introduced between the source 102 and the first mirror 104.

In one implementation of the oblique illuminator in FIG. 1, the projected numerical aperture in a plane normal to the illuminating line on the target 108 is 0.7, which is somewhat small. It is desirable to have a higher numerical aperture, such as 0.85, or 0.95, or even higher, to reduce the linewidth of the line illumination. However, if the design depicted in FIG. 1 is used, then increasing the numerical aperture results in a dramatic increase in the residual aberrations caused by the cylindrical mirrors. In other words, the aspherical term for the acylinder increases dramatically. Even so, the residual aberrations still cannot be completely corrected.

Figure 2:
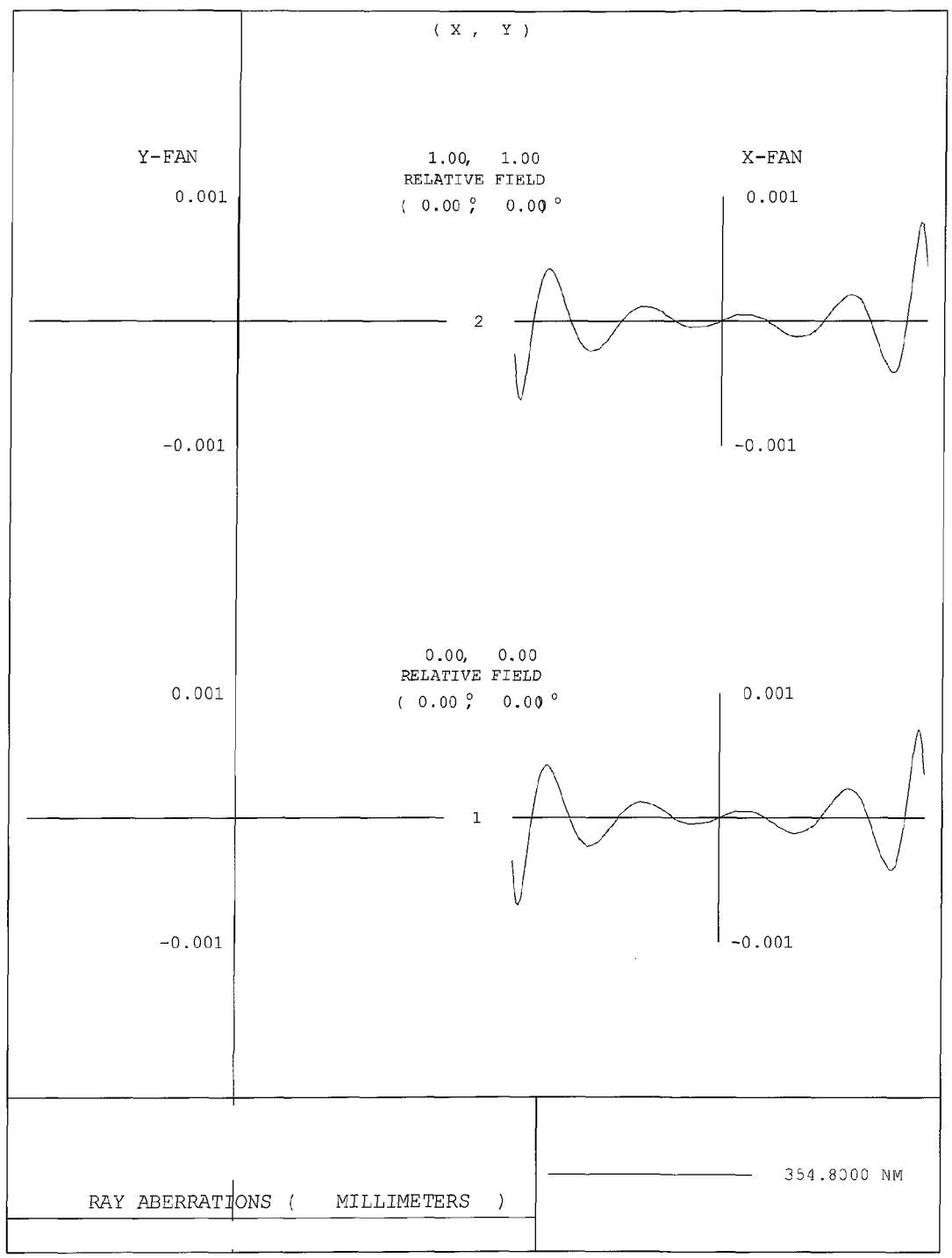
FIG. 2 shows ray fan plots of the oblique illuminator of FIG. 1 with a relatively large numerical aperture.

FIG. 2 shows ray fan plots of the oblique illuminator of FIG. 1 with a relatively large numerical aperture of 0.85. The ray fan plots show ray aberrations as a function of pupil coordinate. As seen by the X-FAN plots on the right side of FIG. 2, substantial ray aberrations are present in the x-dimension. For a numerical aperture of 0.85, the aspheric sag is relatively larger (larger than 2 microns), and extra aspherical terms are needed to reduce the residual aberrations.

Figure 3A:
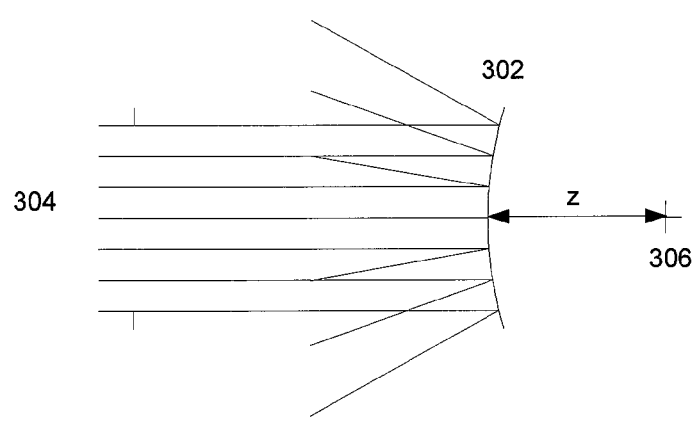
FIGS. 3a, 3b, and 3c illustrate the ray focusing properties of parabolic, spherical, and elliptical mirrors, respectively, in the plane of the page.
Figure 3B:
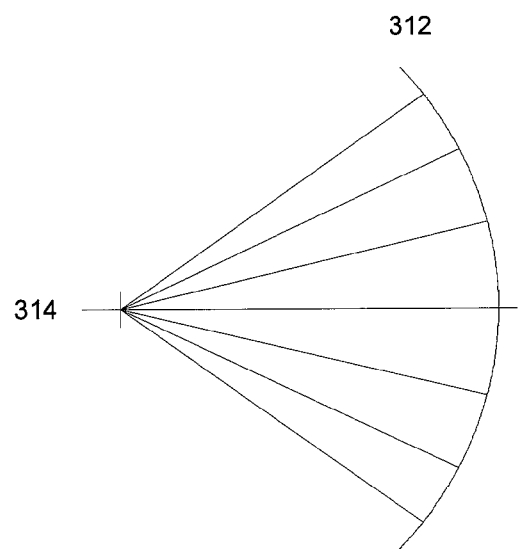
Figure 3C:
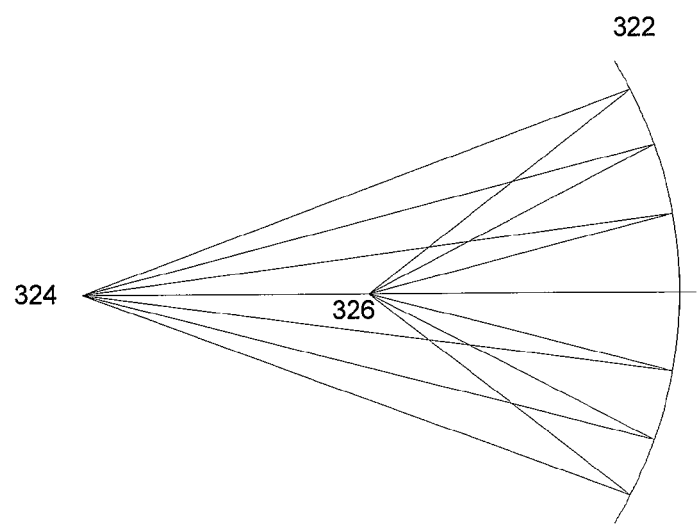

FIGS. 3a, 3b, and 3c illustrate the ray focusing properties of parabolic, spherical, and elliptical mirrors, respectively, in the plane of the page. These diagrams are described to provide a foundation to understand the embodiments of the invention disclosed herein.

Per FIG. 3a, a parallel beam of incident light 304 is reflected from the convex surface of the parabolic mirror 302. The rays of the reflected light diverge as if originating from a virtual point source 306 behind the mirror 302. The virtual point source 306 is at the focal point of the parabolic shape of the mirror surface 302. As such a convex parabolic mirror may form a perfect virtual image at its focal point which is a distance z=R/2 from the vertex of the parabola, where R is the radius of curvature of the parabola.

If 302 is a cylindrical mirror with a parabolic cross-section, a virtual line image 306 will be formed. As such, a concave parabolic cylindrical mirror may be used to form a perfect virtual line image for a collimated input light.

Per FIG. 3b, incident light from a point source 314 is reflected from concave surface of a spherical mirror 312. In the illustrated case, the point source 314 is at the center of the spherical shape of the mirror surface 312. In this case, the reflected rays converge back onto the point source 314. As such, a concave spherical mirror may be used to form a perfect image of an object located at its center.

Similarly, a perfect line image can be formed by placing a line object 314 at the center line of a cylindrical mirror 312. As such, a cylindrical mirror may be used to form a perfect line image of a line object at its center.

Per FIG. 3c, incident light from a point source is reflected from a concave surface of an elliptical mirror 322. The point source may be at a first focal point of the elliptical shape of the mirror surface 322. The reflected light converges onto a second focal point of the elliptical shape. The point source may be at the farther focal point 324, and the reflected rays may converge at the nearer focal point 326, or vice versa. As such, a concave elliptical mirror may be used to form an image at one focal point of the ellipse when an object is placed at the other focal point.

Similarly, a perfect line image can be formed at one focal line 326 of a a cylindrical mirror 322 with an elliptical profile by placing a line object 324 at the other focal line. As such, a cylindrical mirror with an elliptical profile may be used to form a perfect line image by placing a line object at one of its focal line.

Figure 4A:
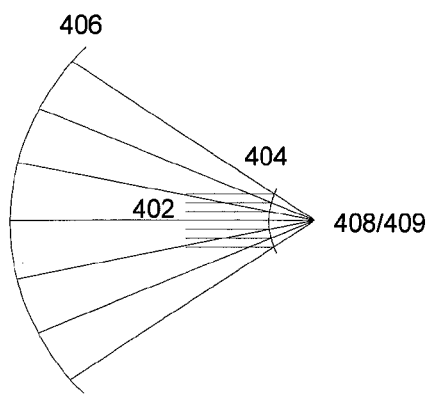
FIG. 4a is a projected view of a dual-mirror configuration in accordance with an embodiment of the invention.

FIG. 4a is a projected view of a first dual-mirror configuration in accordance with an embodiment of the invention. A projected view in another orientation of this first dual-mirror configuration is shown in FIG. 4c. This dual-mirror configuration includes a first mirror 404 which is a convex parabolic cylindrical mirror and a second mirror 406 which is a concave spherical cylindrical mirror.

The first mirror 404 has a reflective convex surface shaped as a cylinder where the projected profile of the cylinder is parabolic. In FIG. 4a, the first mirror 404 is parabolic in the plane of the page, and the axis of the cylinder is normal to the plane of the page. The parabolic cylinder has a virtual focal line 408 which is normal to the plane of the page.

The second mirror 406 has a reflective concave surface shaped as a cylinder where the projected profile of the cylinder is spherical. In FIG. 4a, the second mirror 406 is spherical in the plane of the page, and the axis 409 of the cylinder is normal to the plane of the page. In particular, the axis 409 of the spherical cylinder 406 is coincident with the virtual focal line 408 of the parabolic cylinder 404.

A beam of light from a light source 402 reflects from the reflective convex surface of the first mirror 404 to the second mirror 406. The light source 402 may be, for example, an ultraviolet wavelength laser. The light is reflected from the reflective concave surface of the second mirror 406 converges to its axis 409 (which is also the virtual focal line 408 of the first mirror 404). The axis 409 lies on the surface of the target substrate 410 such that an illuminated line segment is formed on the target surface.

Figure 4B:
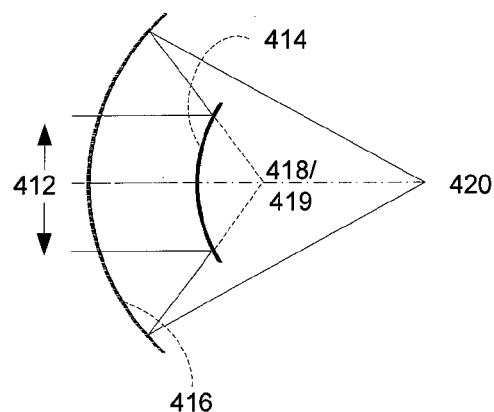
FIG. 4b is a projected view of a second dual-mirror configuration in accordance with an embodiment of the invention.
Figure 4C:
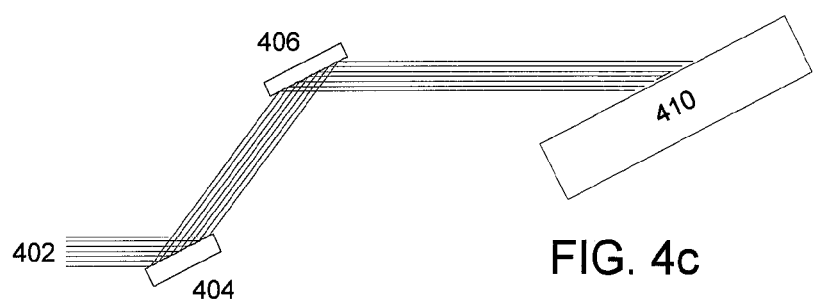
FIG. 4c is a projected view of the first dual-mirror configuration of FIG. 4a in a plane perpendicular to the viewing plane as in FIG. 4a in accordance with an embodiment of the invention.
Figure 4D:
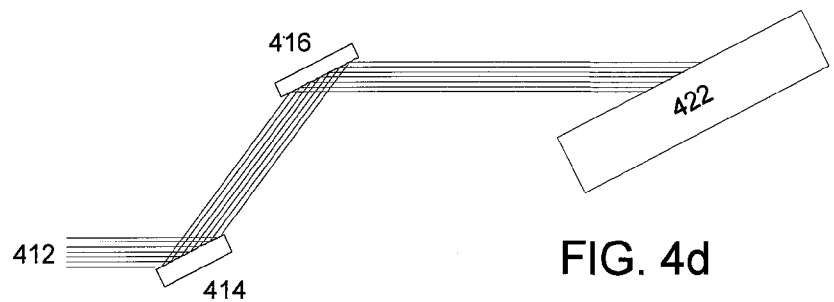
FIG. 4d is a projected view of the second dual-mirror configuration of FIG. 4b in a plane perpendicular to the viewing plane as in FIG. 4b in accordance with an embodiment of the invention.

FIG. 4b is a projected view of a second dual-mirror configuration in accordance with an embodiment of the invention. A projected view in another orientation of this second dual-mirror configuration is shown in FIG. 4d. This dual-mirror configuration includes a first mirror 414 which is a convex parabolic cylindrical mirror and a second mirror 416 which is a concave elliptical cylindrical mirror.

The first mirror 414 has a reflective convex surface shaped as a cylinder where the projected profile of the cylinder is parabolic. In FIG. 4b, the first mirror 414 is parabolic in the plane of the page, and the axis of the cylinder is normal to the plane of the page. The parabolic cylinder has a virtual focal line 418 which is normal to the plane of the page.

The second mirror 416 has a reflective concave surface shaped as a cylinder where the projected profile of the cylinder is elliptical. In FIG. 4b, the second mirror 416 is elliptical in the plane of the page. A first (in this case, nearer) focal line 419 of the elliptical cylinder is normal to the plane of the page. In particular, the first focal line 419 of the elliptical cylinder 406 is coincident with the virtual focal line 418 of the parabolic cylinder 414. A second (in this case, farther) focal line 420 of the elliptical cylinder is also normal to the plane of the page.

A beam of light from a source 412 reflects from the reflective convex surface of the first mirror 414 to the second mirror 416. The light is reflected from the reflective concave surface of the second mirror 416 converges to the second focal line 420. The second focal line 420 lies on the surface of the target substrate 422 such that an illuminated line segment is formed on the target surface.

Note that while FIG. 4b depicts the embodiment where the nearer focal line of the elliptical cylinder is coincident with the focal line of the parabolic cylinder, and where the farther focal line of the elliptical cylinder is coincident with the surface of the target substrate. In another embodiment, the nearer and farther focal lines may be reversed. In other words, in this other embodiment, the farther focal line of the elliptical cylinder is coincident with the focal line of the parabolic cylinder, and the nearer focal line of the elliptical cylinder is coincident with the surface of the target substrate.

Applicants have determined that the radius of curvature of the convex reflecting and concave reflecting surfaces are independent of the index of refraction of the medium in between the two reflective surfaces. Hence, in the embodiments described above in relation to FIGS. 4a through 4d, the medium between the two mirrors may be air, or any other light-transmitting medium, such as, for example, fused silica, or calcium fluoride.

In one implementation, where the design may be constructed using two separate reflective mirror elements, and the medium may be air. In this implementation, each mirror element may include a supporting substrate with a reflective layer on its surface. Such an implementation is described below in relation to FIGS. 5 through 7. In another implementation, the design may be constructed using a single light-transmitting solid piece with two reflecting surfaces. Such an implementation is described below in relation to FIGS. 8 through 11.

Figure 6:
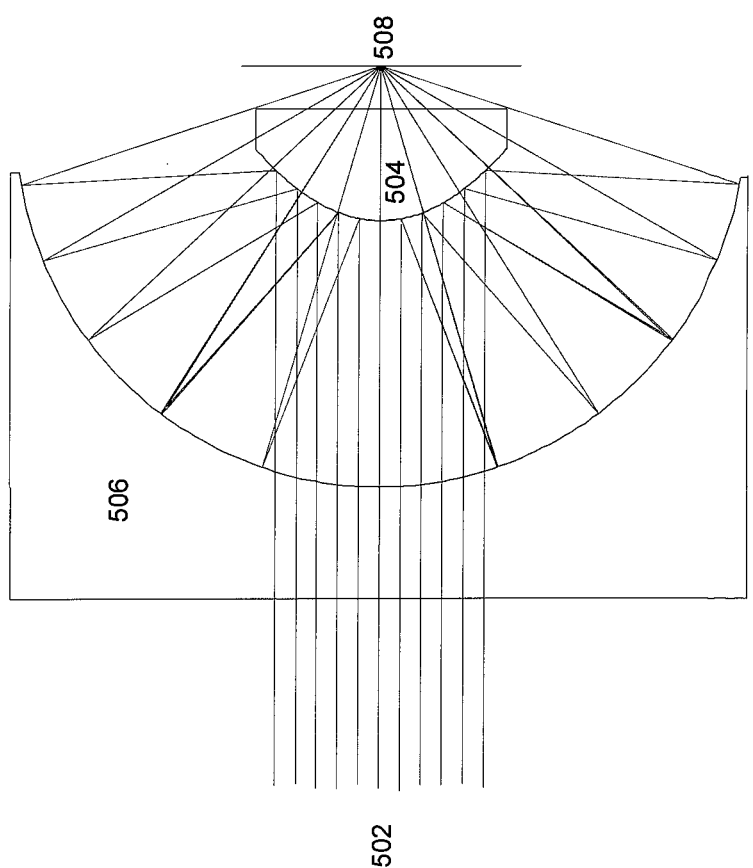
FIG. 6 shows another projected view of the illuminator of FIG. 5 in accordance with an embodiment of the invention.

FIG. 5 shows an optical layout of a two-mirror broadband oblique illuminator for an optical inspection system in accordance with an embodiment of the invention. A projected view of the illuminator is depicted in FIG. 6. In addition, a lens listing for this illuminator is provided in Appendix A. The illuminator depicted in FIGS. 5 and 6 includes a light source 502, a first mirror 504, and a second mirror 506 which is a separate optical element from the first mirror 504. The medium between the two mirrors may be air, for example, or any other light-transmitting medium, such as, for example, fused silica.

The first (bottom) mirror 504 is a convex parabolic cylindrical mirror (i.e. a convex cylindrical mirror having a projected parabolic profile) with a virtual focus line which lies above (or on) the image plane (i.e. the plane of the target surface). The second (top) mirror 506 is a concave elliptical cylindrical mirror (i.e. a concave cylindrical mirror having a projected elliptical profile) with a first focus line which is coincident with the virtual focus line of the first mirror 504 and a second focus line which lies on the surface of the target substrate 508.

Figure 7:
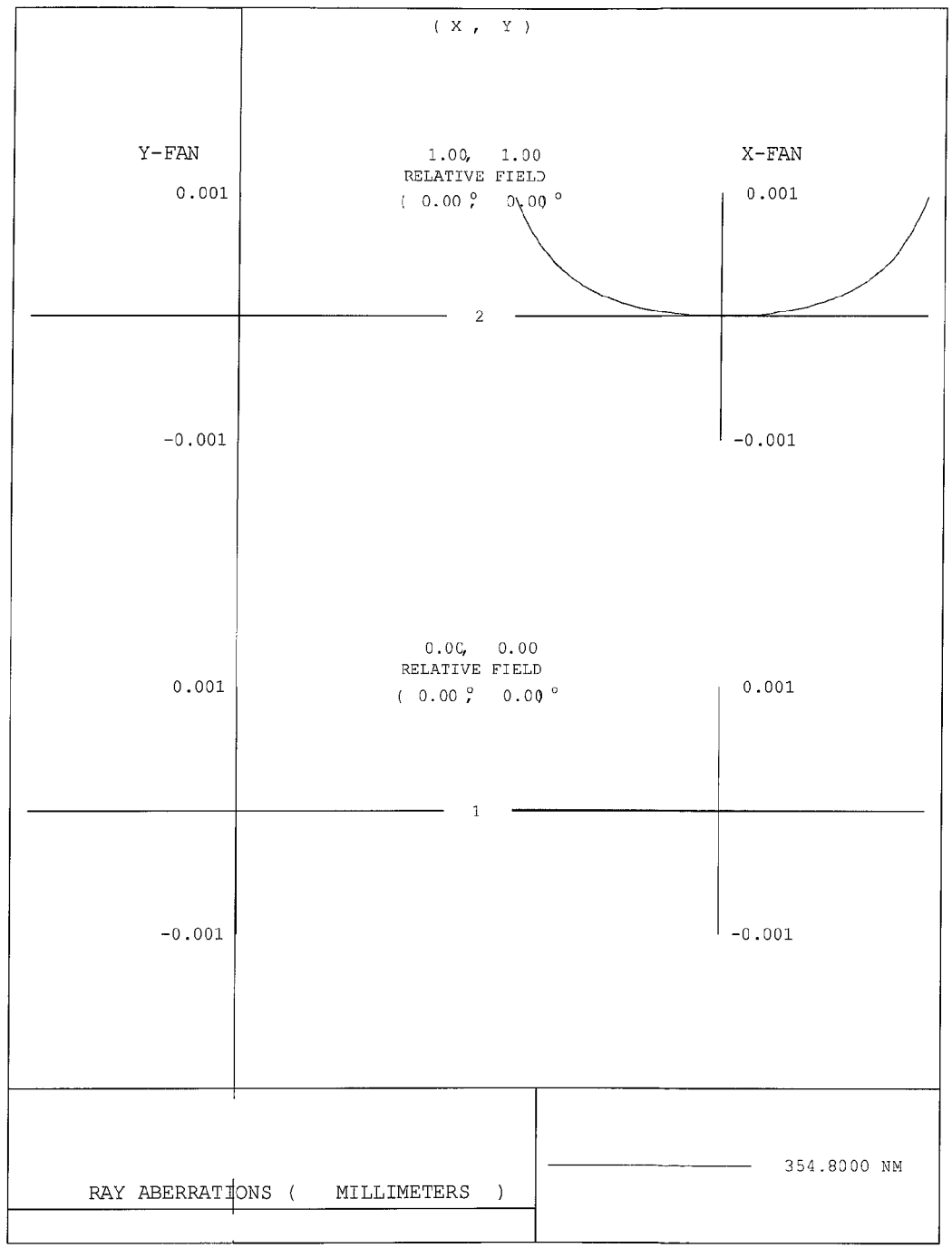
FIG. 7 shows ray fan plots of the broadband oblique illuminator of FIGS. 5 and 6 in accordance with an embodiment of the invention.

FIG. 7 shows ray fan plots of the two-mirror broadband oblique illuminator of FIGS. 5 and 6 in accordance with an embodiment of the invention. As seen in FIG. 7, there is an absence of geometrical aberrations using this illuminator design.

As described previously, the second mirror 506 can be a concave spherical cylindrical mirror, in which case, the virtual focus line formed by the first mirror 504 lies on the image plane which is the target substrate surface 508, the two focal lines of the second mirror 506 will overlap and lie on the top surface of the target substrate 508.

In addition to the illuminator, the optical inspection system includes a detector 510 and a processing system 512. The detector 510 may be configured to detect light scattered, diffracted, and/or reflected from the illuminated line segment on the surface of the target substrate and to generate light-detection signals based on the detected light. The processing system 512 may be configured with electronic circuitry to process the light-detection signals from the detector to generate image data and a computer (including one or more processors, memory, and computer-readable program code) to process the image data to detect defects on the surface of the target substrate.

Figure 8:
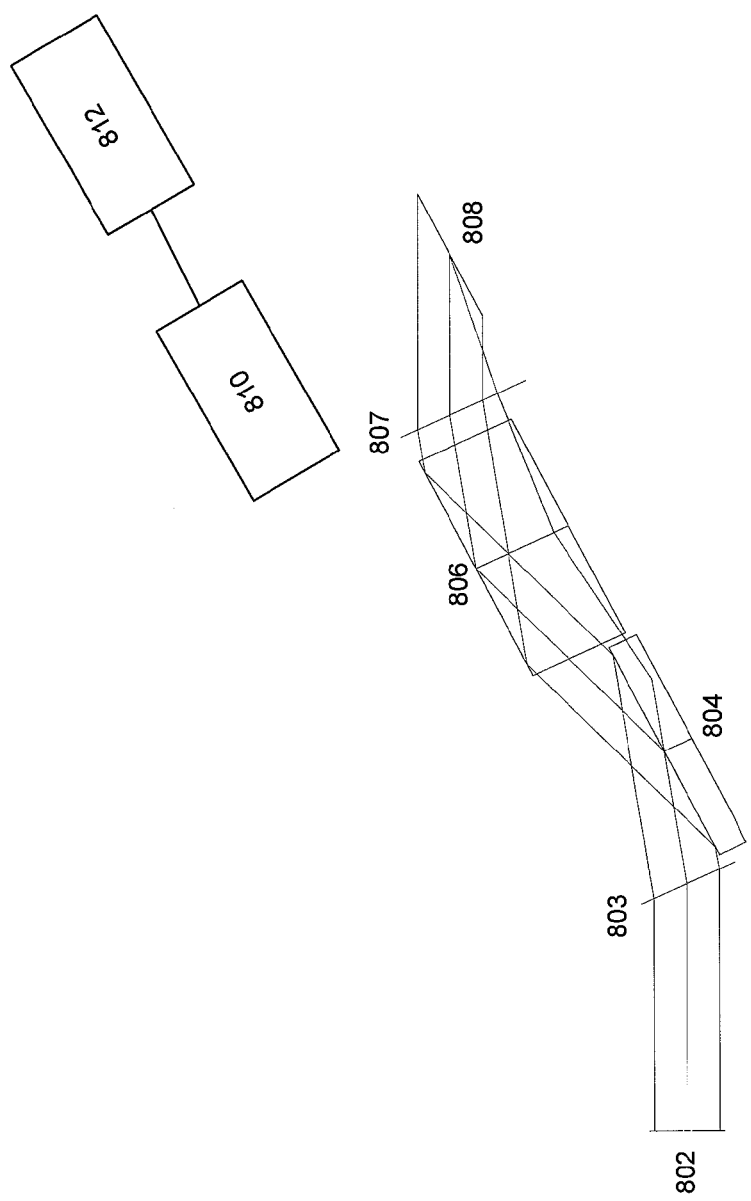
FIG. 8 shows a projected view of a one-piece dual-reflector broadband oblique illuminator for an optical inspection system in accordance with an embodiment of the invention.
Figure 9:
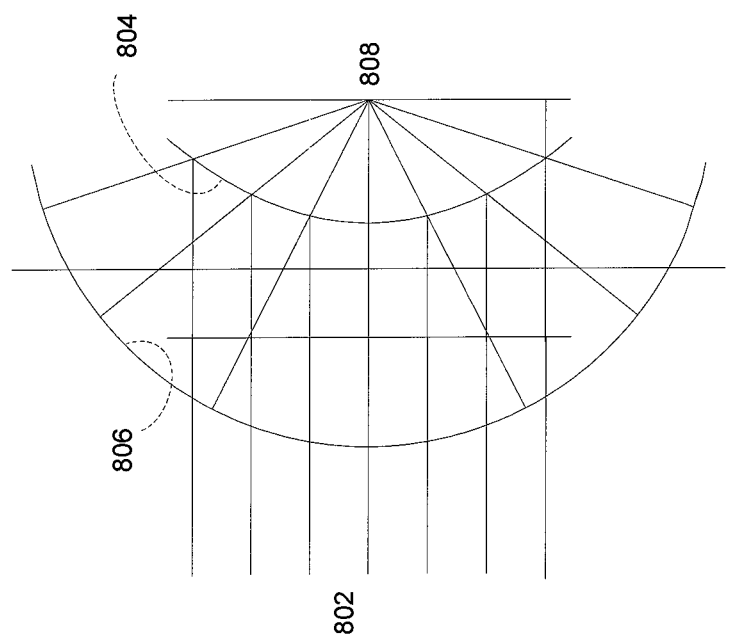
FIG. 9 shows another projected view of the illuminator of FIG. 8 in accordance with an embodiment of the invention.

FIG. 8 shows a line-spread view of a one-piece dual-reflecting broadband oblique illuminator for an optical inspection system in accordance with an embodiment of the invention. In this embodiment, the material between the two reflecting surface may not be air and may have a refractive index of greater than 1.0, A projected view of this illuminator is depicted in FIG. 9. In addition, a lens listing for this illuminator is provided in Appendix B. The illuminator depicted in FIGS. 8 and 9 includes a light source 802 and a single-piece (one-piece) dual reflector which includes an entry surface 803, a first reflecting surface 804, a second reflecting surface 806, and an exit surface 807. The one-piece dual reflector may be made out of a rigid light-transmitting material, such as glass, which is preferably insensitive to thermal variations. This design is substantially achromatic and is insensitive to the glass selection.

A light beam emitted from the source 802 enters the one-piece dual reflector at the entry surface 803 and travels to the first (bottom) surface 804. The first surface 804 is a convex parabolic cylindrical surface (i.e. a convex cylindrical surface with a projected parabolic profile) with a virtual focus line which lies just slightly above or directly on the image plane (i.e. the plane of the target surface). The light beam is refracted by the entry surface 803, then reflected from the first surface 804 and travels to the second (top) surface 806, finally the light beam refracted again by the exit surface 807 and form a line image on top of the target substrate surface 808. The reflection from the first surface 804 may be by total internal reflection.

The second surface 806 can be a concave spherical surface mirror (i.e. a concave cylindrical surface with spherical curvature) with a focus line which is coincident with the virtual focus line of the first surface 804 and which also lies on the surface of the target substrate 808. Note that a cylindrical surface with a spherical curvature is a special case of a cylindrical surface with elliptical curvature, where the two focal lines of the elliptically-curved cylinder are coincident (i.e. the same). The light beam is reflected from the second surface 806 and travels to the target substrate surface 808. The reflection from the second surface 806 may be by total internal reflection.

The light beam exits the one-piece dual reflector at the exit surface 807 and illuminates a line segment on the surface of the target substrate 808. Note that the entrance surface 803 and exit surface 807 are preferably parallel to each other and are preferably normal to the formed line image on the target surface. The oblique (non-normal) angle of illumination may vary depending on the implementation. In one specific implementation, the illumination may be at an incident angle of 64 degrees, where the incident angle of normal illumination is defined as zero degrees.

Similar to the previous embodiment as in FIGS. 5 to 7, the second surface 806 can also be an elliptical cylindrical surface, in which case, the virtual focal line of the first surface 804 will coincide with one focal line of the second surface 806, while the other focal line of the second surface 806 will lie on the top surface of the target substrate 808.

Note that for the one-piece dual reflector there is no need for a mirror substrate to support the bottom reflecting surface. This is because the bottom reflecting surface is a bottom surface of the single piece in this embodiment. As such, the single-piece optics may be placed very close to the image plane (i.e. the plane of the target surface). Using this design, a high numerical aperture of 0.9, or 0.95, or even closer to 1.0 may be achievable.

In contrast, an embodiment which requires the bottom mirror to be supported by a mirror substrate may not be positioned so close to the image plane. Since the incoming light beam has a limited beam width, this would limit the numerical aperture such that high numerical apertures may be difficult to achieve.

The radius of curvature ($R_1$) of the parabolic cylindrical reflecting surface 804 satisfies Equation 1.

$$R_1 = -\frac{\frac{\phi}{2}}{\tan\left(\frac{\sin^{-1} NA}{2}\right)} \quad \text{(Equation 1)}$$

where $\phi$ represents the diameter of the incoming beam, and NA is the target numerical aperture of the laser line beam.

The radius of curvature ($R_2$) of the spherical cylindrical reflecting surface 806 satisfies the Equation 2.

$$R_2 = \frac{R_1}{2} + d \quad \text{(Equation 2)}$$

where d represents the vertical distance between the two reflecting surfaces.

Applicants have determined that the values of $R_1$ and $R_2$ are independent of the index of refraction of the medium between the two reflective surfaces. As such, the tolerance on the index of refraction is insensitive. (In the extreme case, it can be air. However, in the case where the medium between the two reflecting surfaces is air, extra substrates are needed to support the two reflecting surfaces.)

In addition to the illuminator, the optical inspection system includes a detector 810 and a processing system 812. The detector 810 may be configured to detect light scattered, diffracted, and/or reflected from the illuminated line segment on the surface of the target substrate and to generate light-detection signals based on the detected light. The processing system 812 may be configured with electronic circuitry to process the light-detection signals from the detector to generate image data and a computer (including one or more processors, memory, and computer-readable program code) to process the image data to detect defects on the surface of the target substrate.

Figure 10:
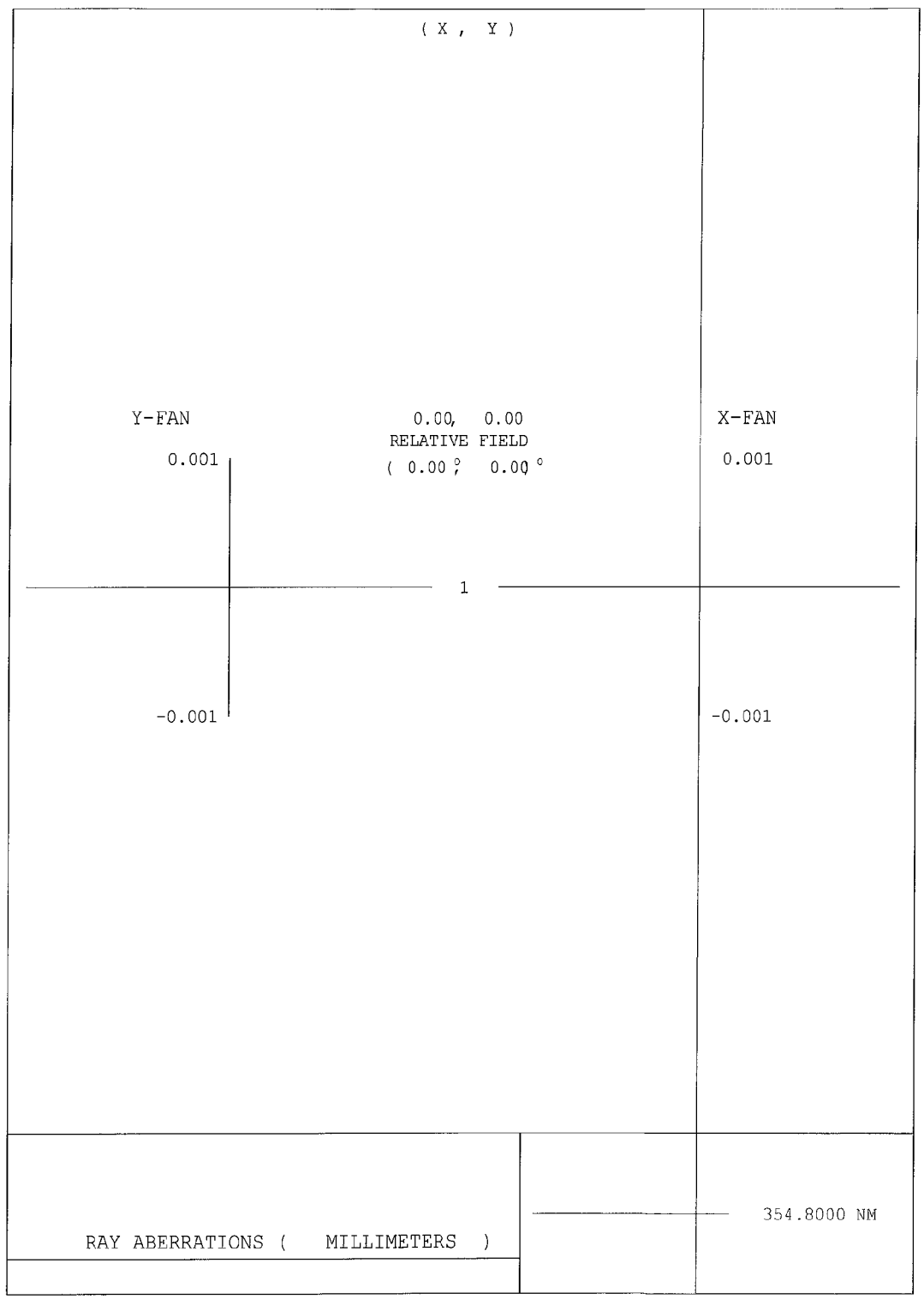
FIG. 10 shows ray fan plots of the illuminator of FIGS. 8 and 9 in accordance with an embodiment of the invention.

FIG. 10 shows ray fan plots of the illuminator of FIGS. 8 and 9 in accordance with an embodiment of the invention. As seen in FIG. 10, a perfect line without geometrical aberration may be formed on the surface of the target substrate.

Figure 11:
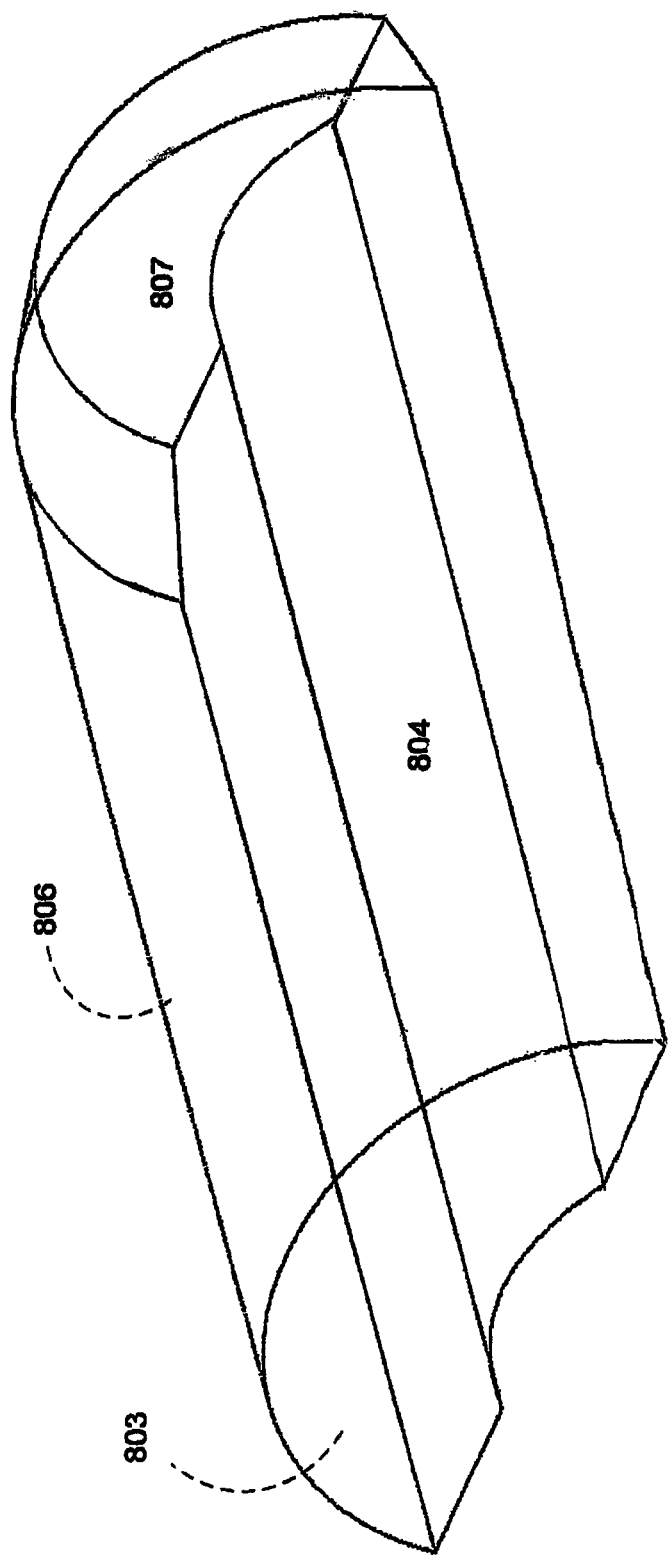
FIG. 11 shows a perspective view of an implementation of a one-piece dual-reflecting optical element in accordance with an embodiment of the invention.

FIG. 11 shows a perspective view of an implementation of a one-piece dual-reflecting optical element in accordance with an embodiment of the invention. As seen in FIG. 11, the one-piece dual-reflecting optical element includes an entry surface 803, a first (bottom) surface 804, a second surface 806, and an exit surface 807.

Figure 12:
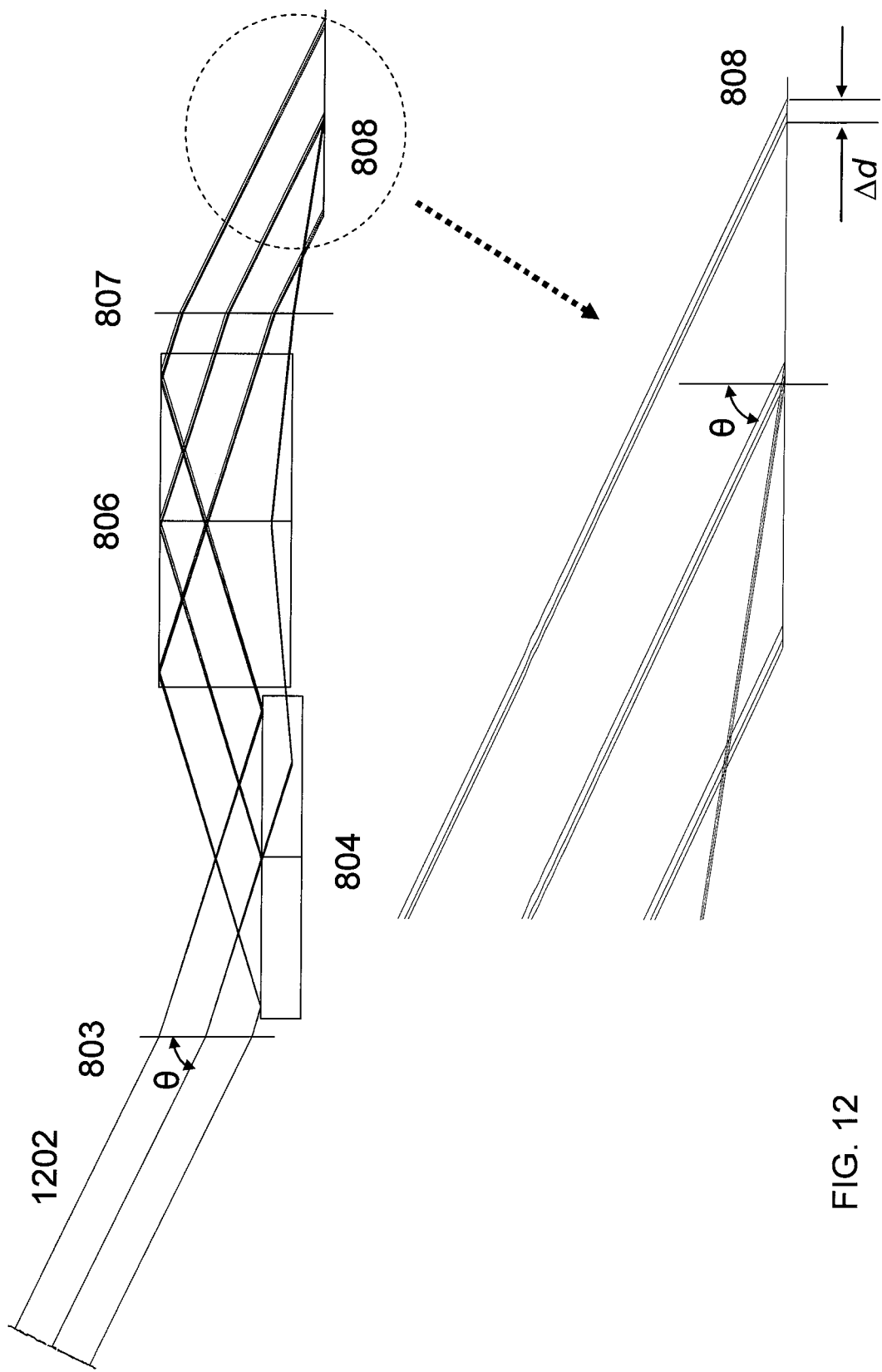
FIG. 12 is an optical layout of a light beam being focused by the optical element of FIGS. 8 to 11 in accordance with an embodiment of the invention.

Advantageously, this illuminator design is achromatic. As such, the width of the spectral band will not affect the linewidth of the final beam profile. Applicants have further determined that the line will indeed spread due to the index of refraction variation at different wavelengths, where the color spread ($\Delta d$) along the non-powered direction of the optics on the target substrate plane 808 satisfies Equation 3, as shown in FIG. 12.

$$\Delta d = t\left(\tan\left(\sin^{-1}\frac{\sin(\frac{\pi}{2}-\theta)}{n_2}\right) - \tan\left(\sin^{-1}\frac{\sin(\frac{\pi}{2}-\theta)}{n_1}\right)\right)\tan\theta \quad \text{(Equation 3)}$$

where t represents the distance between the entrance port (surface) 803 and the exit port (surface) 807, and $n_1$ and $n_2$ are the indices of refraction at the outer extreme wavelengths, and $\theta$ is the illumination incident angle for the light beam 1202 entering the entrance port 803.

One advantage of using the single-piece reflecting design is that, since the bottom reflecting surface does not need to have a substrate, the whole line forming optical piece may be placed very close to the imaging plane, which is the top surface of the target substrate.

If the illumination incident angle $\theta$ (as in FIG. 12) is high enough to satisfy Equation 4, then total internal reflection will occur on the two reflection surfaces 804 and 806, no reflecting coating is required on this two surfaces.

$$n\cos\left(\sin^{-1}\left(\frac{\cos\theta}{n}\right)\right) > 1 \quad \text{(Equation 4)}$$

where n is the refractive index for the longest wavelength within the illuminating spectrum.

However, in a lot of cases, the first and second reflecting surfaces (804 and 806, respectively) are still coated with reflective coatings. One advantage is that coating both cylindrical surfaces of the one-piece optical element minimizes phase retardation issues related with the implementation of total internal reflection (TIR) reflections.

APPENDIX A

| Lens Listing for Dual Mirror Design. | | | |
|---|---|---|---|
| RDY | THI | RMD | GLA |
| >OBJ: INFINITY | INFINITY | | |
| STO: INFINITY | 144.133222 | | |
| 2: INFINITY 0.000000 | | | |
| XDE: 0.000000 | YDE: 0.000000 | | ZDE: 0.000000 |
| ADE: −64.000000 | BDE: 0.000000 | | CDE: 0.000000 |
| 3: INFINITY | −19.000000 | REFL | |
| XTO: | | | |
| RDX: 7.93069 | | | |
| K: −1.000000 | | | |
| A: 0.000000E+00 | B: 0.000000E+00 | | C: 0.000000E+00 |

APPENDIX A-continued

Lens Listing for Dual Mirror Design.

```
  D: 0.000000E+00
  CUM: 0.000000       THM: 8.000000        GLM:
4: INFINITY           0.000000
5: INFINITY          30.000000             REFL
  XTO:
  RDX: 26.01552
  K: -0.017640
  A: 0.000000E+00    B: 0.000000E+00      C: 0.000000E+00
  D: 0.000000E+00
  XDE: 0.000000      YDE: 38.955773       ZDE: 0.000000
  ADE: 0.000000      BDE: 0.000000        CDE: 0.000000
  CUM: 0.000000      THM: 8.000000        GLM:
  IMG: INFINITY      0.000000
  XDE: 0.000000      YDE: 61.509115       ZDE: 0.000000
  DAR
  ADE: 0.000000      BDE: 0.000000        CDE: 0.000000
```

SPECIFICATION DATA

| | |
|---|---|
| EPD | 15.00000 |
| DIM | MM |
| WL | 354.80 |
| REF | 1 |
| WTW | 1 |
| XAN | 0.00000  0.00120 |
| YAN | 0.00000  0.00120 |
| WTF | 1.00000  1.00000 |
| VUX | 0.00000  0.00000 |
| VLX | 0.00000  0.00000 |
| VUY | 0.50000  0.50000 |
| VLY | 0.50000  0.50000 |
| POL | N |

INFINITE CONJUGATES

| | |
|---|---|
| EFL | 0.1000E+19 |
| BFL | -0.1000E+19 |
| FFL | -0.1000E+19 |
| FNO | 0.6667E+17 |

AT USED CONJUGATES

| | |
|---|---|
| RED | ********** |
| FNO | -0.6667E+17 |
| OBJ DIS | 0.1000E+14 |
| TT | 0.1000E+14 |
| IMG DIS | 30.0000 |
| OAL | 125.1332 |

PARAXIAL IMAGE

| | |
|---|---|
| HT | 0.2094E+14 |
| THI | -0.1000E+19 |
| ANG | 0.0012 |

ENTRANCE PUPIL

| | |
|---|---|
| DIA | 15.0000 |
| THI | 0.0000 |

EXIT PUPIL

| | |
|---|---|
| DIA | 15.0000 |
| THI | -163.1332 |

APPENDIX B

Lens Listing for Single Piece Design.
lfc_t2 aut_z4d7e4 73.8 2x

| | RDY | THI | RMD | GLA |
|---|---|---|---|---|
| >OBJ: | INFINITY | INFINITY | | |
| 1: | INFINITY | 0.000000 | | |
| 2: | INFINITY | 130.540062 | | |
| STO: | INFINITY | 0.000000 | | |
| 4: | INFINITY | 0.000000 | | |

```
  XDE: 34.960149    YDE: 0.000000       ZDE: 108.319408
  ADE: 0.000000     BDE: 64.000000      CDE: 0.000000
```

APPENDIX B-continued

Lens Listing for Single Piece Design.
lfc_t2 aut_z4d7e4 73.8 2x

```
5:  INFINITY           0.000000
    XDE: 0.000000      YDE: 0.000000      ZDE: 0.000000
    ADE: 0.000000      BDE: 0.000000      CDE: 0.000000
6:  INFINITY           0.000000
    XDE: -99.807942    YDE: 0.000000      ZDE: 0.000000
    GLB G5
    ADE: 0.000000      BDE: 0.000000      CDE: 0.000000
7:  INFINITY           0.000000           SILICA_SPECIAL
    XDE: 0.000000      YDE: 0.000000      ZDE: 0.000000
    DAR
    ADE: 0.000000      BDE: -90.000000    CDE: 0.000000
8:  9.94547            0.000000    TIRO   SILICA_SPECIAL
    GL2:
    YTO:
    RDX: INFINITY
    K: -1.000000
    A: 0.000000E+00    B: 0.000000E+00    C: 0.000000E+00
    D: 0.000000E+00
    XDE: -84.341764    YDE: 0.000000      ZDE: -4.972736
    GLB G5
    ADE: 0.000000      BDE: 0.000000      CDE: 0.000000
    CEM:               CIN:               CTH: 0.0000
9:  17.90000           0.000000    TIRO   SILICA_SPECIAL
    GL2:
    YTO:
    RDX: INFINITY
    K: 0.000000
    A: 0.000000E+00    B: 0.000000E+00    C: 0.000000E+00
    D: 0.000000E+00
    XDE: -42.776198    YDE: 0.000000      ZDE: -17.900000
    GLB G5
    ADE: 0.000000      BDE: 0.000000      CDE: 0.000000
    CEM:               CIN:               CTH: 0.0000
10: INFINITY           0.000000
    XDE: 16.768249     YDE: 0.000000      ZDE: 0.000000
    DAR
    ADE: 0.000000      BDE: 90.000000     CDE: 0.000000
11: INFINITY          17.900000
12: INFINITY           0.000000
    IMG: INFINITY      0.000000
    XDE: 42.776198     YDE: 0.000000      ZDE: 0.000000
    DAR
    ADE: 0.000000      BDE: 0.000000      CDE: 0.000000
```

SPECIFICATION DATA

| | |
|---|---|
| EPD | 14.40000 |
| DIM | MM |
| WL | 354.80 |
| REF | 1 |
| WTW | 1 |
| INI | SZ |
| XAN | 0.00000 |
| YAN | 0.00000 |
| WTF | 1.00000 |
| VUX | 0.50000 |
| VLX | 0.50000 |
| VUY | 0.00000 |
| VLY | 0.00000 |
| POL | Y |
| PFR | 1.0000 |
| PTP | 0.0000 |
| POR | 90.0000 |
| PRO | LIN |
| PCS | COL |
| PST | IDL |
| RVT | N |

REFRACTIVE INDICES

| GLASS CODE | 354.80 |
|---|---|
| SILICA_SPECIAL | 1.476108 |

INFINITE CONJUGATES

| | |
|---|---|
| EFL | 3.3688 |
| BFL | -5.7735 |

APPENDIX B-continued

Lens Listing for Single Piece Design.
lfc_t2 aut_z4d7e4 73.8 2x

| FFL | 236.9877 |
| --- | --- |
| FNO | 0.2339 |
| IMG DIS | 0.0000 |
| OAL | 238.8595 |

PARAXIAL IMAGE

| HT | 0.0000 |
| --- | --- |
| ANG | 0.0000 |

ENTRANCE PUPIL

| DIA | 14.4000 |
| --- | --- |
| THI | 130.5401 |

EXIT PUPIL

| DIA | 0.4557 |
| --- | --- |
| THI | −5.6669 |

What is claimed is:

1. An apparatus for inspecting a target substrate, the apparatus comprising:
an oblique illuminator comprising
a light source emitting a light beam,
a first reflective surface having a convex cylindrical shape with a projected parabolic profile which is configured to reflect the light beam from the light source and which defines a focal line, and
a second reflective surface having a concave cylindrical shape with a projected elliptical profile which is configured to reflect the light beam from the first reflective surface and which defines first and second focal lines,
wherein the focal line of the first reflective surface is coincident with the first focal line of the second reflective surface,
wherein the second reflective surface is configured such that the second focal line of the second reflective surface lies on a surface of the target substrate such that a line segment is illuminated on the surface of the target substrate, and
wherein the first reflective surface comprises a bottom surface of an optical element, and the second reflective surface comprises a top surface of the optical element; and
a detector configured to detect light diffracted from the surface of the target substrate and to generate light-detection signals based on detected light.

2. The apparatus of claim 1, further comprising:
a processing system configured to process the light-detection signals from the detector to generate image data and to process the image data to detect defects on the surface of the target substrate.

3. The apparatus of claim 2, wherein the first and second focal lines are a same line.

4. The apparatus of claim 1, wherein the optical element is formed of a rigid light-transmitting material, and wherein the first and second reflective surfaces are configured to reflect the light beam by total internal reflection.

5. The apparatus of claim 1, wherein the rigid light-transmitting material comprises glass.

6. The apparatus of claim 1, wherein the light source comprises an ultraviolet wavelength laser.

7. A method for inspecting a target substrate, the method comprising:
illuminating a line on a surface of a target substrate by
emitting a light beam from a light source,
reflecting the light beam from a first reflective surface having a convex cylindrical shape with a projected parabolic profile which defines a focal line, and
reflecting the light beam from a second reflective surface having a concave cylindrical shape with a projected elliptical profile which defines first and second focal lines, wherein the focal line of the first reflective surface is coincident with the first focal line of the second reflective surface, wherein the first reflective surface comprises a bottom surface of an optical element, and the second reflective surface comprises a top surface of the optical element;
detecting light diffracted from the surface of the target substrate; and
generating light-detection signals based on detected light.

8. The method of claim 7, wherein the second reflective surface is configured such that the second focal line of the second reflective surface lies on a surface of the target substrate.

9. The method of claim 8, wherein the first and second focal lines are a same line.

10. The method of claim 7, wherein the optical element comprises a rigid light-transmitting material, and wherein the reflection from the first and second reflective surfaces is by total internal reflection.

11. The method of claim 7, wherein the rigid light-transmitting material comprises glass.

12. The method of claim 7, wherein the light source comprises an ultraviolet wavelength laser.

* * * * *